US009766228B2

(12) United States Patent
Puschmann et al.

(10) Patent No.: US 9,766,228 B2
(45) Date of Patent: Sep. 19, 2017

(54) COATED FIBER SCAFFOLD FOR THREE DIMENSIONAL CELL CULTURE OF NEURAL CELLS

(75) Inventors: Till Benjamin Puschmann, Göteborg (SE); Milos Pekny, Göteborg (SE); Carl Zanden, Göteborg (SE); Johan Liu, Västra Frölunda (SE)

(73) Assignee: 3Dtro AB, Gothenburg (SE)

( * ) Notice: Subject to any disclaimer, the term of this patent is extended or adjusted under 35 U.S.C. 154(b) by 746 days.

(21) Appl. No.: 14/117,567

(22) PCT Filed: May 16, 2012

(86) PCT No.: PCT/SE2012/050537
§ 371 (c)(1), (2), (4) Date: Jul. 3, 2014

(87) PCT Pub. No.: WO2012/158120
PCT Pub. Date: Nov. 22, 2012

(65) Prior Publication Data

US 2014/0315235 A1 Oct. 23, 2014

(30) Foreign Application Priority Data

May 17, 2011 (SE) ...................................... 1130042

(51) Int. Cl.

| | |
|---|---|
| ***C12N 5/00*** | (2006.01) |
| ***C12N 5/02*** | (2006.01) |
| ***G01N 33/50*** | (2006.01) |
| ***C12M 1/24*** | (2006.01) |
| ***C12M 1/32*** | (2006.01) |
| ***C12M 1/00*** | (2006.01) |
| ***C12M 1/12*** | (2006.01) |
| ***C12N 5/079*** | (2010.01) |

(52) U.S. Cl.
CPC ......... *G01N 33/5058* (2013.01); *C12M 23/08* (2013.01); *C12M 23/12* (2013.01); *C12M 23/20* (2013.01); *C12M 25/14* (2013.01); *C12N 5/0618* (2013.01); *C12N 2513/00* (2013.01); *C12N 2533/10* (2013.01); *C12N 2533/32* (2013.01); *C12N 2533/54* (2013.01)

(58) Field of Classification Search
None
See application file for complete search history.

(56) References Cited

U.S. PATENT DOCUMENTS

| | | | | |
|---|---|---|---|---|
| 5,266,476 A | 11/1993 | Sussman et al. | | |
| 2005/0095695 A1* | 5/2005 | Shindler | B82Y 5/00 | 435/285.1 |
| 2007/0082393 A1* | 4/2007 | Lodhi | A61L 27/38 | 435/325 |
| 2010/0098902 A1* | 4/2010 | Kotov | B05D 7/54 | 428/105 |

FOREIGN PATENT DOCUMENTS

| | | |
|---|---|---|
| WO | WO-2006/094076 A2 | 9/2006 |
| WO | WO-2009/114138 A2 | 9/2009 |

OTHER PUBLICATIONS

Carlberg et al., Biomed. Mater., 4:1-7 (2009).*
Lee et al., Biomater., 30:4325-4335 (2009).*
Kotwal et al., Biomater., 22:1055-1064 (2001).*
Xie et al., ACS Nano, 3(5): 1151-1159 (2009).*
Christopherson et al., Biomater., 30:556-564 (2009).*
Cullen et al., J. Neural Eng., 5:374-384 (2008).*
Mazzatenta et al., J. Neurosci., 27(26):6931-6936 (2007).*
Murugan et al., Tiss. Eng., 12(3):435-447 (2006).*
Orza et al., ACS Nano., 5(6):4490-4503 (2011).*
Quigley et al., Adv. Mater., 21:4393-4397 (2009).*
Xie et al., Adv. Funct. Mater., 19:2312-2318 (2009).*
Xie et al., Nanoscale, 2:35-44 (2010).*
Badami et al., Biomater., 27:596-606 (2006).*
Bakhru et al., Integr. Biol., 3:1207-1214 (2011).*
Xie et al.,Biomater., 30:354-362 (2009).*
Baiguera et al., In vitro astrocyte and cerebral endothelial cell response to electrospun poly(ϵ-caprolactone) mats of different architecture, J. Mater. Sci. Mater Med., 21:1353-62 (2010).
Delgado-Rivera et al., Increased FGF-2 secretion and ability to support neurite outgrowth by astrocytes cultured on polyamide nanofibrillar matrices, Matrix Biol., 28(3):137-47 (2009).
Gupta et al., Nanostructured biocomposite substrates by electrospinning and electrospraying for the mineralization of osteoblasts, Biomaterials, 30(11):2085-94 (2009).
Hurtado et al., Robust CNS regeneration after complete spinal cord transection using aligned poly-L-lactic acid microfibers, Biomaterials, 32(26):6068-79 (2011).
International Search Report for corresponding international application No. PCT/SE2012/050537, mailing date Sep. 7, 2012.
Lanfer et al., Directed growth of adult human white matter stem cell-derived neurons on aligned fibrillar collagen, Tissue Eng. Part A, 16(4)1103-13 (2010).
Mahairaki et al., Nanofiber matrices promote the neuronal differentiation of human embryonic stem cell-derived neural precursors in vitro, Tissue Eng. Part A, 17(5-6):855-63 (2011).
Nartker et al., Electrospun cellulose nitrate nanofibers, J. Nanosci. Nanotechnol., 10(9):5810-3 (2010).
Yoo, et al., "Surface-functionalized electrospun nanofibers for tissue engineering and drug delivery," Advanced Drug Delivery Reviews 61, 1033-1042 (2009).

(Continued)

*Primary Examiner* — Thomas J Visone
(74) *Attorney, Agent, or Firm* — Marshall, Gerstein & Borun LLP

(57) ABSTRACT

The invention relates to a biocompatible scaffold for three dimensional cultivation of cells, said scaffold comprise one or more fibers randomly oriented to form a scaffold with open spaces for cultured cells. The one or more fibers are also coated with a bio-active coating and have a diameter of 100-3000 nm.

19 Claims, 11 Drawing Sheets

(56) References Cited

OTHER PUBLICATIONS

Zander et al., Surface-modified nanofibrous biomaterial bridge for the enhancement and control of neurite outgrowth, Biointerphases, 5(4):149-58 (2010).

"3D Cell Culture: An Early-Stage Oncology Drug Discovery Tool," 3D Biomatrix, 1600 Huron Parkway, Building 520, $2^{nd}$ Floor, Ann Arbor, MI 48109-2590, White Paper, 13 pages (2012).

* cited by examiner

1a

1b 5a 5b 5c 5d 5e 5f 5g

7a

7b

7c a b c

9a

9b

9c

10a

10b

10c 11a 11b 11c

COATED FIBER SCAFFOLD FOR THREE DIMENSIONAL CELL CULTURE OF NEURAL CELLS

This application is the U.S. national phase of International Application No. PCT/SE2012/050537, filed 16 May 2012, incorporated by reference, which claims priority benefit of Swedish Patent Application No. 1130042-3, filed 17 May 2011.

TECHNICAL FIELD

The present invention relates to biotechnology particularly in particular cell culture systems, more particularly three dimensional neural cell culture systems using fiber scaffolds.

BACKGROUND ART

Many biological processes and metabolic functions of individual cell types are particularly difficult to study in vivo due to the vast array of different cells communicating between each other. Further, in many cases technical as well as ethical considerations do not allow in vivo experimentation. Therefore, in vitro cell culture systems have been developed to allow to specific study of individual cell types and cell types particularly difficult to study in vivo, such as cells derived from human tissue. The most common cell culture systems use a two dimensional surface such as plastic or glass to grow cells upon. They provide a highly artificial cell culture environment where cells are forced to grow in ways they never do in the body.

There is a growing recognition of the disadvantages of the conventional in vitro cell culture systems, namely the lack of an adequate preservation of the biological functions and complexity present in vivo.

In order for a cell to receive correct signals for proliferation, differentiation, migration or programmed cell death, the spatial cues and topologically defined position of specific cell membrane receptors, attachment molecules or release of humoral factors are essential. These signal transduction pathways are stimulated and influenced by the organization and structure of the cell cytoskeleton. The architecture of which is comprised of and defined by a vast array of cell-cell and cell-matrix contacts, as well as cytoskeleton-receptor structure. All of these cell function-determining factors are highly altered in conventional two dimensional cell culture systems due to the altered cell shape and cell cytoskeleton morphology, which lead to aberrant cytoskeletal compositions.

Hence in recent years, research has become more and more focused on cell culture systems, which would mimic the three dimensional environments found in vivo.

A number of approaches to establish three dimensional cell culture systems have been undertaken with the major aim to mimic the extracellular matrix (ECM) and configuration and to give structural, dimensional stability to the cells in culture.

Recent work has demonstrated the major influence and importance of unique micro- and nano-environments in spatial organization of tissue like patterns of cells and their signal transduction as well as differentiation functions (Mueller-Klieser 1997; Cukierman, Pankov et al. 2001; Walpita and Hay 2002).

Amongst the most predominant culture methods are gel and collagen systems, nanofiber scaffolds and porous scaffolds that aim to promote three dimensional cell growth (for review see Lee, Cuddihy et al. 2008). All of these platforms developed to date, however, have distinct disadvantages such as cell aggregation, low cell survival or experimental limitations.

Only few attempts have been made to develop functional three dimensional cell culture systems using fiber scaffolds. These scaffolds generally consist of a fibrous structure. The benefits of such three dimensional fibrous matrices include a high surface-to-volume ratio and a structure similar to the in vivo collagen and elastin network. So far, there is only one product commercially available, which offers a three dimensional platform constructed of nanofiber scaffolds (Cell-treat™). These fibers, however, come aligned in well defined spatial distribution and without treatment of the fiber surface such as coating with extracellular matrix molecules.

Fiber alignment appears to have very specific effects on cell cultures, mainly on migration and morphology, which are not desired in the present invention.

US patent US20070269481 describes a 'Biomemetic Scaffold' consisting of aligned nanofibers with or without crosslinked coating of the fibers. However, the alignment is not desired for many cell culture systems.

Further US patent US20060263417 describes 'Electrospun blends of natural and synthetic polymer fibers as tissue engineering scaffolds'. Similarly, U.S. Pat. No. 7,704,740 'Nanofibrillar structure and applications including cell and tissue culture' describes the manufacturing of random oriented electrospun nanofibers with the aim to proliferate cell and tissue cultures.

SUMMARY OF THE INVENTION

An object of the present invention is to provide a novel specially coated biocompatible scaffold for three dimensional cultures of cells providing a cell culture matrix that supports neural cell growth in a three dimensional fashion in a designed milieu optimized for individual cell types to be cultured, inducing cell morphologies resembling the true cell morphology, and preserving the cell metabolism, receptor activation and protein expression in a way which resembles the true situation in the brain (in vivo).

The term "fiber" used herein refers to a fiber made of a non-cytotoxic polymer which may be comprised of but is not limited to polyurethane fibers.

The term "biocompatible fiber" refers to fibers as described within this description, examples and claims, which are comprised of a material that is non-cytotoxic.

The term "scaffold" as used herein refers to a network of fibers consisting of one or more fibers spun on top of each other using electrospinning methods.

The term "randomly oriented fibers" as used herein refers to a fiber scaffold consisting of electrospun fibers that have not been actively aligned or that do not follow any designed pattern of orientation to each other.

The term "coated fiber scaffold for three dimensional neural cell culture" as used herein refers to a structure comprised of one or more random oriented fibers, coated with bio-active substrates as described in the claim section, creating an environment supporting the growth of neural cell types in a three dimensional fashion.

The term "aligned fibers" as used herein refers to a fiber scaffold that consists of one or more fibers that are oriented in parallel to each other during the electrospinning process.

The term plastic material refers to polymers selected from the group consisting of Polystyrene (PS), Poly acrylo nitrile (PAN), Poly carbonate (PC), polyvinylpyrrolidone, polybutadiene (PVP), Polyvinyl butyral (PVB), Poly vinyl chloride (PVC), Poly vinyl methyl ether (PVME), poly lactic-co-glycolic acid (PLGA), poly(l-lactic acid), polyester, polycaprolactone (PCL), poly ethylene oxide (PEO), polyaniline (PANI), polyflourenes, polypyrroles (PPY), poly ethylene dioxythiophene (PEDOT) or a mixture of those.

The term "bio-active substrate" refers to for example poly-D-lysine, laminin, poly-L-ornithine and other similar compounds as well as their functional peptide groups.

The term "coated fibers" refers to fibers as described above, the coat may be for example poly-L-ornithine+laminin or poly-D-lysine.

The term "substrate" as used herein refers to any surface such as—but not limited to—plastic or glass, on which the fibers or fiber scaffolds are deposited onto.

The term "container" as used herein means any container suitable for culturing cells in for example a plate, dish or tube.

The term "electrical conductive material" as used herein refers to an electrically conductive material that is suitable for cells to grow on.

The term "electrical stimulation through AC and/or DC" refers to a process in which the cells are being exposed to a mild electrical current of either alternating current (AC) or direct current (DC). The current may be introduced into the scaffold or applied via the cell culture media or other suitable components of the cell culture system.

MODES FOR CARRYING OUT THE INVENTION

According to a general embodiment of the invention a biocompatible scaffold for three dimensional cultivation of cells comprises one or more fibers randomly oriented to form a scaffold with open spaces for cultured cells, and a bio-active coating on the one or more fibers, wherein the randomly oriented fibers have a diameter in the range of 100-3000 nm. In another embodiment is the diameter of the fibers about 900-1500 nm, and in yet another embodiment is the diameter of the fibers in the range of 180-500 nm or 500-900 nm.

In one embodiment of the invention, the one or more fibers of the scaffold are electrospun polymer fibers.

In one embodiment the one or more electrospun polymer fibers, may comprise a polymer (plastics) selected from the group consisting of polystyrene (PS), poly acrylo nitrile (PAN), poly carbonate (PC), polyvinylpyrrolidone, polybutadiene (PVP), polyvinyl butyral (PVB), poly vinyl chloride (PVC), poly vinyl methyl ether (PVME), poly lactic-co-glycolic acid (PLGA), poly(l-lactic acid), polyester, polycaprolactone (PCL), poly ethylene oxide (PEO), polyaniline (PANI), polyflourenes, polypyrroles (PPY), poly ethylene dioxythiophene (PEDOT) or mixtures thereof.

In yet another embodiment, the one or more fibers comprise polyether-based polyurethane.

In another embodiment the porosity (air to fiber volume) corresponds to 60-95% or 65-75% open spaces and in yet another embodiment may the porosity consist of 70-90% open spaces.

In one embodiment the bioactive coating comprise at least one bio-active substrate selected from collagen I, poly-D-lysine, poly-L-ornithine, and laminin.

In yet another embodiment the bio-active coating is a mixture of poly-L-ornithine and laminin attached to the fibers by incubation of the fibers in a solution containing the bio-active substrates.

In another embodiment the bio-active peptide is laminin co-electrosprayed with the electrospun polyether polyurethane fibers during manufacturing.

In one embodiment the vertical thickness of the fiber scaffold is about 200 micrometers or less.

In yet another embodiment the scaffold of the present invention further has an electrically conductive materials disposed between the fiber polymer and the bio-active coating.

In yet another embodiment the fibers has a sputter coating of titanium or platinum or gold beneath the bio-active coating, however, other conductive materials may also be used.

In another embodiment the sputter coating has a thickness of less than about 200 nanometers.

In one embodiment of the invention, the randomly oriented fiber scaffolds are placed upon or integrated with electrically conductive material in the form of aligned fibers. This set up can for example be used to investigate the wound closure process of neural cells of an electrically induced wound. The electrically conductive fibers can be attached to a signal analyzing device that monitors changes by impedance spectroscopy due to cell coverage and other cell activities. When neural cells proliferate or migrate into the wound area, changes in the impedance spectra will allow to measure the speed and extent of migration/proliferation occurring as the wound is closed i.e. the speed and extent to which the cells repopulate the wound area.

In another embodiment of the invention, the randomly oriented fiber scaffolds are placed upon or integrated with electrically conductive material in the form of aligned fibers acting as electrodes. This set up can for example be used as an in vitro scratch wound device. The conductive fibers are applied with elevated field towards the corresponding counter electrode to achieve cell death due to electrocution within a defined area of the fiber scaffolds. The usage of the invention allows generation of well-defined electrical wound areas with precise dimensions to investigate cellular behavior after wound infliction in a fibrous in vitro environment offered by the randomly oriented fiber scaffold. It is also possible to use lower voltage levels that induce minor currents to study the cell response to electrical stimulation through AC and DC fields in an in vitro environment.

The scaffold according to the various embodiments of the present invention may further comprise aligned fibers, wherein the scaffold comprises a mixture of randomly oriented and aligned fibers.

In yet another embodiment of the invention the randomly oriented fiber scaffolds comprise aligned fibers further having a sputter coating of electrically conductive material.

The fibers in the scaffold described above or in any embodiment may also be plasma treated before coating with bio-active substrates.

In another embodiment the cells to be cultured are selected from the group consisting of astroglia (astrocytes), neurons, oligodendrocytes, neural progenitor cells and Schwann cells. However, any other cell type may also be cultured using the present invention.

In one embodiment freely combinable with other embodiments the scaffold is adapted for the culture of astrocytes.

In another embodiment the bioactive coat is poly-L-ornithine and laminin (POLAM), but other coatings may also be used.

In yet another embodiment freely combinable with other embodiments the fiber diameter is about 900-1500 nm, more preferably about 1000-1400 nm, and most preferably about 1100-1300 nm for the cultivation of astrocytes.

In another embodiment the scaffold is adapted for the culture of neurons.

In this embodiment, the bioactive coat is poly-D-lysine (PDL), however other suitable coatings may be used.

In another embodiment the fiber diameter is about 100-900 nm, more preferably about 200-800 nm, and most preferably 350-500 nm for the cultivation of neurons.

Another object of the present invention is to provide a cell culture system comprising a container to hold cells, cell culture media, and the scaffold described above, the cells are attached to said scaffold disposed within the container.

According to one embodiment the container is for example a test tube, petri-dish or a multi-well plate.

In one embodiment the cell culture system further comprises a substrate, wherein the scaffold is attached to or disposed on a surface of the substrate.

In yet another embodiment of the invention comprise the substrate a glass or plastic surface on which the scaffold is attached or disposed.

In one embodiment of the invention the substrate is a glass or plastic slide, coverslip, or disc.

In another embodiment of the invention the cell culture system further comprise a containment structure of inert material to immobilize the scaffold.

In one embodiment the containment structure is in the shape of a ring or two rings holding the structure in place. However, the containment structure may also be of other shapes.

In one embodiment the inert material of the containment structure may be selected from the group consisting of plastics (polymers) and polytetrafluoroethylene (PTFE), however other materials are not excluded.

Yet another object of the present invention is to provide a method for culturing cells comprising:

seeding a scaffold with cells, adding a culture media; and incubating the resultant 3-dimensional culture under conditions suitable for attachment of the cells to the scaffold and growth of the cells.

In one embodiment said cells are at least one cell type selected from the group consisting of astroglia (astrocytes), neurons, neural progenitor cells, oligodendrocytes, progenitor cells, and Schwann cells.

Another object of the present invention is to provide a method for screening an agent for effects on cells, said method comprise the steps of:

seeding a scaffold according to the invention, culturing cells in the presence and absence of a test agent; and determining effects of the test agent on the cells by comparing cellular events in the cells grown in the presence of the agent versus the absence of the agent.

In one embodiment, determination of the effects of the test agent on the cells is performed by commonly used protein analysis methods, such as, for example, Western blot, Elisa and/or immunohistochemical methods.

In another embodiment other methods to investigate cellular behavior may be used, such as determining gene expression by RNA harvest or morphological changes using transgenic cells expressing fluorescent marker proteins.

The present invention provides a novel and inventive three dimensional cell culture system allowing cells to grow in a three dimensional milieu. The results show that the provided biocompatible scaffold for culture of cells, and method for the same, works very well for neural cell cultures. The present invention gives unexpected results concerning morphology, proliferation and metabolism of the different cell types.

Moreover, the present invention opens up many possibilities to study neural cells and influence of agents on the cells metabolism and behavior in vitro, which reduce the number of animal in vivo models an early stage research.

DETAILED DESCRIPTION OF THE INVENTION

Before the invention is disclosed and described in detail, it is to be understood that this invention is not limited to particular materials or configurations disclosed herein as such configurations and materials may vary. It is also to be understood that the terminology employed herein is used for the purpose of describing particular embodiments only and is not intended to be limiting since the scope of the present invention is limited only by the appended claims.

The present invention will now be described in more detail hereafter with reference to the accompanying examples and figures, in which embodiments of the invention are shown. This invention may, however, be embodied in many different forms and should not be construed as limited to the embodiments set forth herein.

Results

Figure 1:
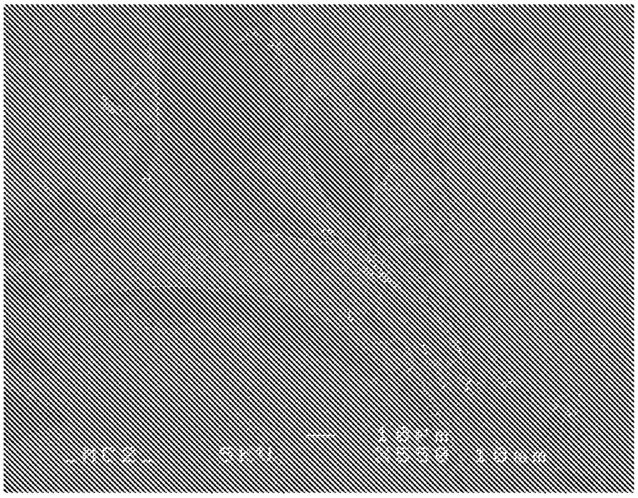
FIG. 1 shows a perspective view of astrocytes grown on a standard two dimensional plastic surface (FIG. 1*a*) or a three dimensional fiber scaffold of the present invention (FIG. 1*b*).
Figure 1:
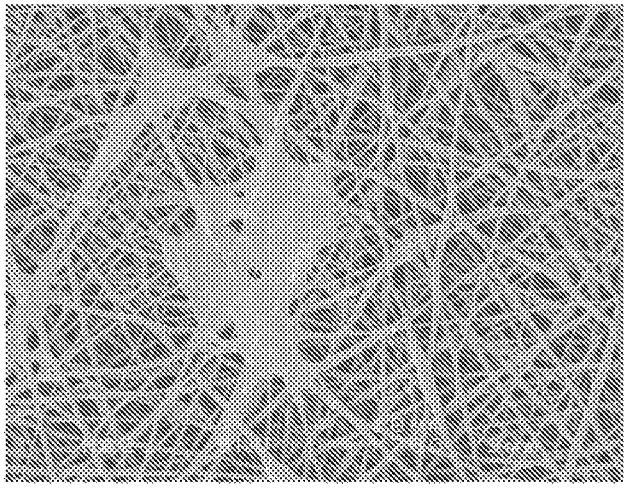

Astrocytes Cultured on Coated Fibers Adapt a Morphology More Resembling the In Vivo Situation FIG. 1*a*, demonstrates effects of the present improved, coated three dimensional scaffold on astrocyte morphology. The cells were cultured on poly-L-ornithine+laminin coated 1200 nm thick electrospun fibers and compared to cells grown on Poly-Lornithine+laminin coated two dimensional plastic cell culture dishes (FIG. 1, *a-b*). Astrocytes grown on the two dimensional plastic cell culture dishes appeared flattened, widespread and polygonal shaped with very symmetrical morphology (FIG. 1*a*). When grown on the three dimensional coated polyurethane fiber scaffold however cells were more complex in morphology with a truly three dimensional shape extending filopodia into the fiber scaffold (FIG. 1*b*).

Figure 2:
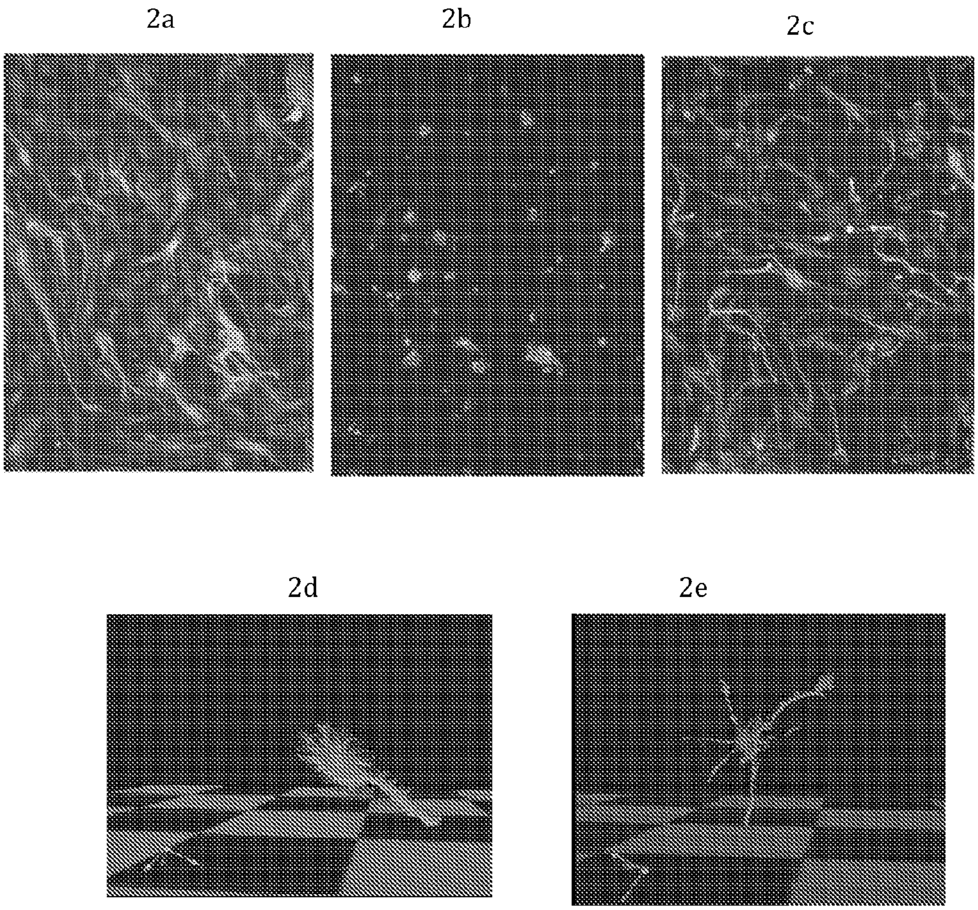
FIG. 2*a-c* show perspective views of the cytoskeleton of astrocytes grown on a standard two dimensional plastic surface (FIG. 2*a*) or a three dimensional uncoated (FIG. 2*b*) or coated (FIG. 2*c*) polyurethane fiber scaffold of the present invention.
FIG. 2*d* and FIG. 2*e* show computer models of a representative astrocyte grown on a standard two dimensional plastic surface (FIG. 2*d*) or a three dimensional coated poly-urethane fiber scaffold of the present invention (FIG. 2*e*).

FIG. 2*a* shows the cytoskeletal staining of astrocytes grown on a planar two dimensional plastic surface. The astrocytes show a flattened morphology.

FIG. 2*b*, shows an astrocyte culture that has been grown on uncoated polyurethane fibers, resulting in loss of viable astrocytes, small protrusion outgrowth and little cell adherence. The nuclei of cells grown on uncoated fibers appear condensed and therefore indicative of dying cells. The present results clearly show that the coating of the fiber scaffold is an integral part of the invention.

FIG. 2*c* shows astrocytes grown on poly-L-ornithine+laminin coated electrospun polyurethane fiber scaffolds. The astrocytes show complex structures, good adhesion and a three dimensional morphology. Cells grown according to the present invention, did not show clusters and cell nuclei were not condensed indicating healthy cells. Computer models of the morphology of astrocytes grown on standard two dimensional cultures (FIG. 2*d*) or astrocytes grown on poly-L-ornithine+laminin coated electrospun polyurethane fiber scaffolds (FIG. 2*e*) are shown.

High resolution confocal and scanning electron microscope images confirmed the highly complex morphology of the astrocyte cytoskeleton when grown on coated fibers as seen in vivo. Cell filopodia have been observed to partially wrap around the fiber mesh and, in some cases, dramatically change direction after extending towards knots of crossing fibers. These data demonstrate the vast improvement of astrocytic cell cultures, now adapting the in vivo like morphology when grown on our coated three dimensional scaffold. To further demonstrate the in vivo-like, true morphology of astrocytes, astrocytes visualised by expressing a fluorescent marker (green fluorescent protein, GFP) were used in the three dimensional cell cultures. The cytoplasmic green fluorescent protein was distributed all over the cells. Confocal z-stack images were taken and the data from individual cells were modelled into a three dimensional volume (FIG. 2*d-e*). There were no significant differences in cell volume (14235±2309 $\mu m^3$ for two dimensional vs. 14930±1784 $\mu m^3$ for three dimensional, n=9 for two dimensional, n=6 for three dimensional, SEM) or cell surface area (15753±2346 $\mu m^2$ for two dimensional vs. 15907±2368 $\mu m^2$ for three dimensional) detected. However, the morphology of three dimensional grown astrocytes was far more complex with long and stellate protrusions (FIG. 2*e*) compared to two dimensional standard astrocyte cultures (FIG. 2*d*) and reminiscent of astrocytes in vivo.

All procedures as described above can also be used for other neural cell types such as neurons, Schwann cells and oligodendrocytes.

Effects of Scaffold Coating on Astrocyte Adhesion and Survival

Figure 3:
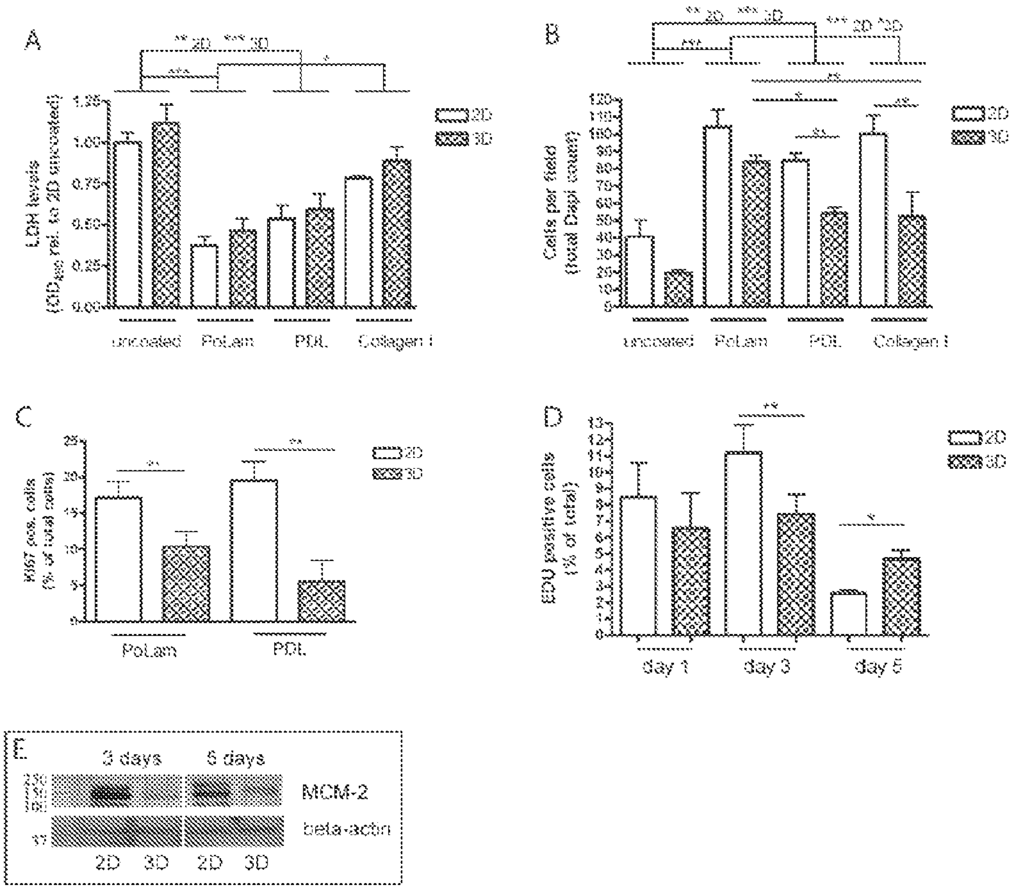
FIG. 3 *a-e* show the effects of scaffold coating on astrocyte adhesion, survival and proliferation.

FIG. 3 demonstrate astrocyte survival 24 h after plating, LDH levels in culture supernatants were measured as an indicator of astrocytic cell death. The inventors tested several different coating methods of the fibers, i.e. poly-D-Lysine, collagen I, poly-L-ornithine+laminin (see under methods), and compared them to standard two dimensional cell cultures. LDH assays were conducted according to manufacturer's guidelines (TaKaRa, Cat# MK401). There were no significant differences in cell death/healthiness between astrocytes grown on two dimensional plates or fiber scaffolds, indicating that the present invention is non-cytotoxic and promotes an at least equal if not higher cell growth environment as standard two dimensional plastic cell culture dishes (FIG. 3A).

Significant differences in cell death were found between the different surface coating variations. The lowest cell survival was found in cultures without surface coating, whereas the best cell survival was achieved after coating the surfaces with poly-L-ornithine+laminin. Therefore, the present coating procedure is a highly important and integral part of the present invention. Further, the inventors demonstrate here that the fibers can be coated with different bio-active substrates to serve the individual needs of certain cell types.

Additional to LDH assays as measurements for survival the inventors counted the number of cells adhering 24 h after plating. Coating the fibers with poly-Lornithine+laminin achieved most astrocyte cell adhesion with no significant differences between the standard two dimensional cell cultures and the fiber scaffolds (FIG. 3B).

Astrocyte Proliferation is Decreased when Grown on the Coated Fiber Scaffold (Limited Astrocyte Proliferation is a Desired Feature of Astrocyte Cultures)

The reactive state of astrocytes is generally defined by increased cytoskeletal protein expression as well as hyper proliferation. Astrocytes in vivo usually only proliferate very little in non-diseased, non-injured tissue, however in vitro in standard two dimensional cell cultures astrocytes became proliferative and reactive. It is therefore desirable to culture astrocytes under less reactive and less proliferative conditions. Immunocytochemistry for the endogenous proliferation marker Ki67 demonstrated lower proliferation and hence less reactivity of astrocytes when cells were grown on the fibers provided by the present dependent of the coating (poly-D-lysine or poly-L-ornithine+laminin), again demonstrating the improvement of the culture system of the present invention to existing two dimensional systems (FIG. 3C).

Since Ki67 is an endogenous proliferation marker and the duration of the presence of the Ki67 antigen is not known, the inventors investigated cell proliferation with an exogenous marker system, EdU-Click-It (Invitrogen), to further confirm changes in astrocyte proliferation between standard two dimensional cell culture systems and our invention. The assay uses a modified nucleoside, EdU (5-ethynyl-2'-deoxyuridine), which is incorporated during DNA synthesis into the cell's nucleus. There were no significant differences at 24 h after plating the cells (FIG. 3D). At 3 days after plating however a significantly lower percentage of astrocytes grown on the coated fiber scaffold was proliferative, similar to the results obtained from Ki67 immunocytochemistry.

Interestingly, at a 5 day time point, three dimensionally grown astrocytes were slightly more proliferative than two dimensionally grown astrocytes. This is possibly due to the fact that at 5 days in culture the two dimensional grown astrocytes were over-confluent and hence entered a state of no further proliferation, due to cell-cell contact mediated inhibition of proliferation. Cells in this stage are known to be non-responsive to most treatments and are therefore not desirable for research experimentation. Cells in the three dimensional system, however, were still responsive and slightly proliferative even 5 days after plating, again demonstrating the vast superiority of our system to other cell culture systems.

To further confirm the altered proliferation rate, Western blot analyses at 3 days and 5 days after cell plating were conducted (FIG. 3E). Proliferation was assessed by for the analysis of MCM-2 protein. MCM-2 is a member of the mini chromosome maintenance complex (MCM) proteins and is a key component of the pre-replication complex involved in the recruitment of other DNA replication proteins. MCM-2 has been shown to be involved in regulation of helicase activity and its upregulation therefore is a sign of increased DNA replication, i.e. proliferation of eukaryotic cells.

At both time points, MCM-2 protein levels were decreased in the three dimensional cell cultures, reflecting the observations from Ki67 and EdU experiments (FIG. 3E). Further, a decrease in the proliferation of astrocytes in two dimensional cultures over time was detected, as it has been shown for EdU uptake.

Figure 4:
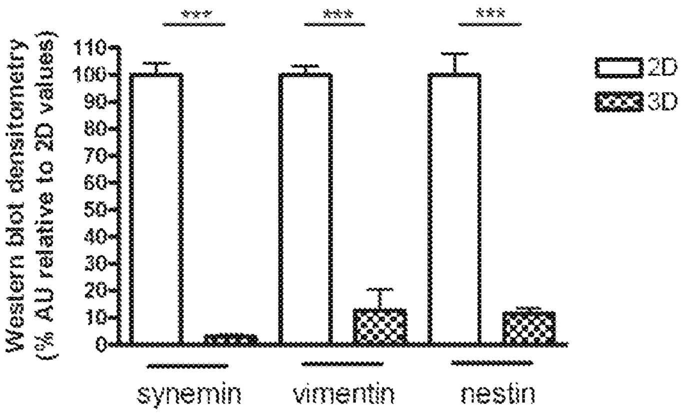
FIG. 4 shows the expression of markers for immature and reactive astrocytes.

Western Blot Analysis of Cytoskeletal Proteins and Stress Proteins Confirm the Improved Cell Culture Conditions for Astrocytes Cultured on Coated Fiber Scaffolds To further confirm the results obtained from immunocytochemistry, the inventors evaluated the actual protein expression levels using Western blot analysis. FIG. 4 shows the densitometry measurements of the chemiluminescence signal derived from the Western blot experiments confirmed significant decrease for vimentin, nestin and synemin proteins when cultured on three dimensional poly-L-ornithine+laminin fibers.

The Western blot analysis confirmed altered cytoskeletal protein expression when astrocytes were grown on the poly-L-ornithine+laminin coated three dimensional scaffold of the present invention. The inventors found differences in synemin, vimentin and nestin expression levels (FIG. 4), which are markers for immature and reactive astrocytes. These markers are known to be upregulated in two dimensional cell cultures, which is an unwanted side effect of the two dimensional culture set-up.

The present invention however overcomes these problems, allowing cell cultures to be more in vivo-like. In astrocytes grown on the coated fiber scaffolds of the present invention, all three proteins mentioned above were significantly less expressed.

The inventors further investigated the stress levels of three dimensional grown astrocytes by Western blot for the heat-shock proteins HSP70 and HSC70. Whilst there were no consistent changes of HSP protein levels between astrocytes from two dimensional and three dimensional cultures, the stress protein HSC70 expression was significantly decreased in cultures grown on the coated fiber scaffolds, further indicating that the present invention offers a much better cell growth environment than the standard two dimensional cell culture systems (Data not shown).

Figure 5H:
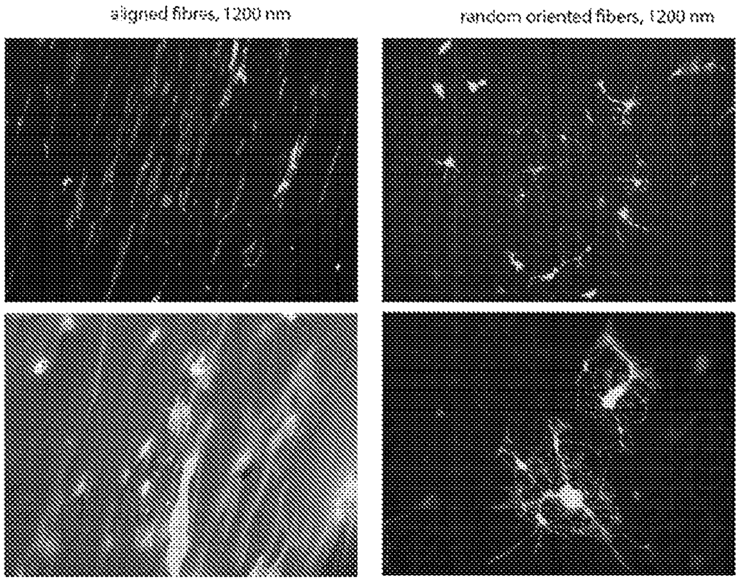
FIG. 5*a-d* show views of astrocytes grown on aligned fiber scaffolds (5*a*, 5*c*, 5*g*) or random oriented fiber scaffolds (5*b*, 5*d* and 5*f*), and the structure of astrocytes in situ (FIG. 5*e*).
Figure 5H:
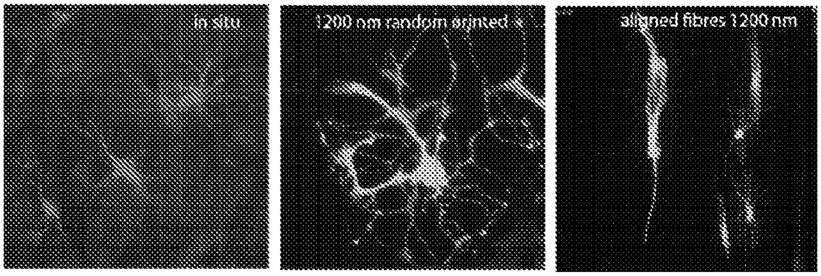
Figure 5:
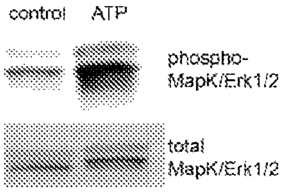

FIG. 5 shows that astrocytes grown on aligned fiber scaffolds (5*a*, 5*c* and 5*g*) will lead to linear, stretched, non in vivo-like cell morphologies compared to astrocytes that are grown on random oriented fiber scaffolds as described within this application (FIGS. 5*b*, 5*d* and 5*f*). FIG. 5*e* shows the morphology of astrocytes in situ, which is much more close to astrocytes grown on the scaffold of the present invention (FIG. 5*f*). FIG. 5*g* shows astrocytes grown on aligned fibers, which does not show the morphology of astrocytes at all. Moreover, FIG. 5*h* shows that the level of MapK/Erk1/2 phosphorylation in astrocytes grown on the scaffold of the present invention is increased upon addition of ATP. The results clearly show that astrocytes grown on the scaffold of the present invention is functional and grown under minimized stress but with full ability to response to activity triggering stimuli, the MapK/Erk1/2 phosphorylation in astrocyte cultures was analyzed by Western blotting after exposure to 100 μM ATP for 1 h following serum deprivation for 4 h. Treatment with ATP leads to a strong activation of the MapK/Erk1/2 signaling cascade in astrocytes grown on the 1200 nm, PoLam-coated scaffolds.

Other Neural Cell Types Grown on the Fiber Scaffold:

Neuronal cultures of primary neuronal cells often are susceptible to contaminations by astrocytes. Given the decreased proliferation ratio of astrocytes in the three dimensional cell culture system, neuronal cell cultures would be much easier to be cultured without unwanted astrocytes contaminating the cultures.

The effect of poly-L-ornithine+laminin coated three dimensional scaffolds on neuronal cell growth was determined. Cortical neurons were seeded on two dimensional poly-L-ornithine+laminin coated glass cover slips and three dimensional poly-L-ornithine+laminin coated fibers. While it is known that neuronal cultures are much more fragile than astrocytes cultures, surprisingly neuronal three dimensional cultures developed extremely well with neurons growing very long axons wrapping around the fibers. Neurons in two dimensional cultures grew shorter axons and were much more susceptible to handling during experimentations with and handling of the cultures (Data not shown).

Figure 6:
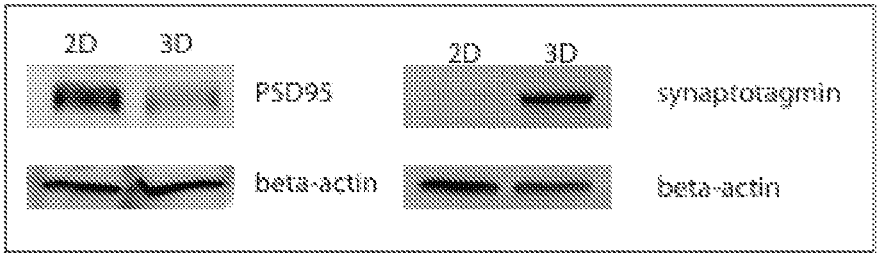
FIG. 6 shows a Western blot of protein expression of PSD95 and synaptotagmin in neuronal cultures.

To further investigate changes in the metabolism of neuronal cultures the inventors conducted Western blot experiments to measure changes in protein expression. Neurons, when grown on the poly-L-ornithine+laminin coated fiber scaffold, showed decreased expression of PSD95 and in contrast an increase in synaptotagmin protein expression (FIG. 6). This demonstrates the significantly different metabolisms between neurons grown in standard two dimensional cell culture systems compared to coated fiber scaffolds.

Figure 7:
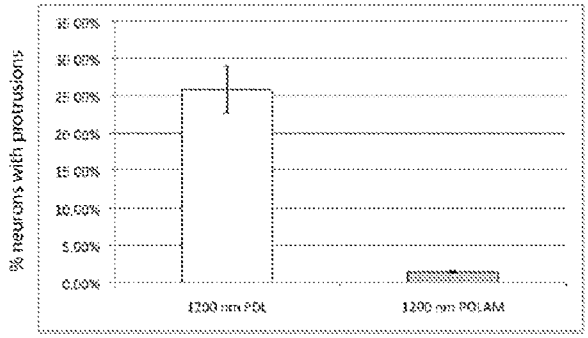
FIG. 7*a* shows a graph demonstrating the percentage neurons with protrusions grown on different coatings on oriented fibers with the diameter of 1200 nm.
FIGS. 7*b* and 7*c* show immunographs of Tuj-1 labelled neurites grown on the respective coat.
Figure 7:
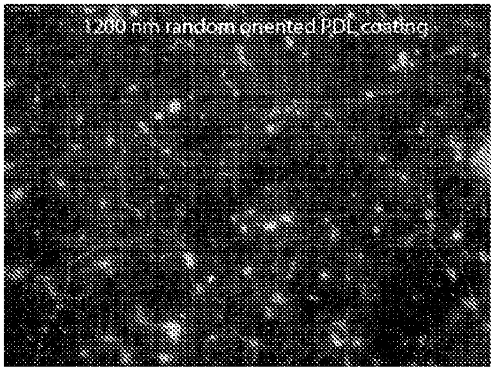
Figure 7:
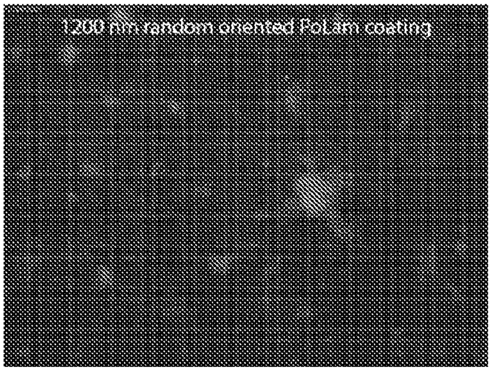

FIG. 7 demonstrates the effect of different types of coatings on the ability of neurons to properly develop cellular protrusion. Freshly isolated hippocampal neurons derived from E16 wild type mice were cultured for 2 days in vitro on either PDL or PoLam coated 1200 nm thick polyurethane based fibers. The cells were labeled with Tuj-1, a neuronal filament marker protein after fixation. Images of neurons were taken and the percentage of neuronal cells with visible protrusions was analyzed. Graph 7*a* and FIG. 7*c* demonstrate that neurons fail to develop proper neuronal protrusions when grown on PoLam coated 1200 nm fibers compared to cells grown on 1200 nm fibers coated with PDL shown in FIG. 7*b* (p value<0.001).

Fiber Diameter is Crucial for Proper Three Dimensional Cell Growth

Figure 8:
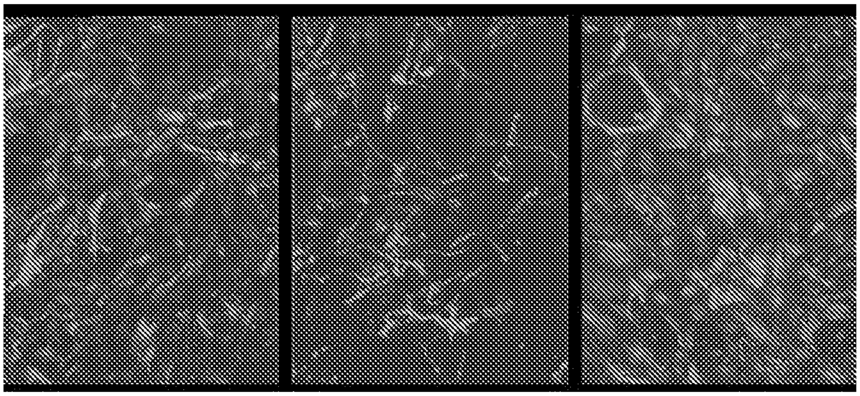
FIG. 8 show a perspective view of the astrocyte cytoskeleton when grown on standard two dimensional cultures (FIG. 8*a*), grown on coated polyurethane fiber scaffolds (FIG. 8*b*) and grown on coated fiber scaffolds, wherein the diameter of the fiber is less than half the diameter of the fibers in the present invention (FIG. 8*c*).

FIG. 8 demonstrates the effects of fiber diameter on cell morphology, the inventors compared astrocytes grown on the 1200 nm fiber diameter fiber scaffolds (FIG. 8*b*) with scaffolds produced of fibers with a diameter of approximately 450 nm (FIG. 8*c*). The fiber scaffolds were coated with poly-L-ornithine and laminine. To evaluate morphology and cytoskeletal protein expression differences, standard immunocytochemistry experiments for the astrocyte cytoskeletal protein GFAP were conducted as described above. The astrocytes grown on the smaller diameter fibers did not properly integrate into the scaffold and appeared morphologically more similar to two dimensional cell cultures (FIG. 8*a*). The cell bodies spread vastly over the surface without filopodia wrapping around the fibers. Further there seemed to be a higher expression of the protein GFAP when grown on the smaller diameter fibers. This finding was unexpected and demonstrates that the ability of astrocytes to intercalate with the right fiber diameter and porosity can change the metabolism of these cells and consecutively their cytoskeletal protein expression. Astrocytes grown on smaller fiber diameters than this invention provides appear to be reactive as judged by their GFAP expression, which is an unwanted effect in drug treatment trials and life sciences. This clearly demonstrates the importance of the right fiber diameter for astroglial cell growth in the present invention.

Figure 9:
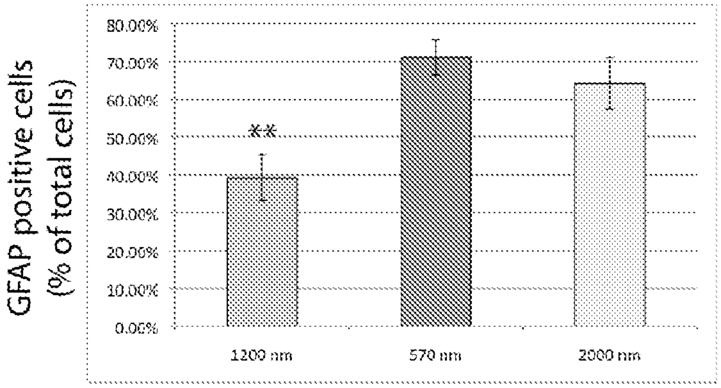
FIG. 9*a* shows a graph demonstrating the differences in GFAP expression in astrocytes grown in cultures with different fiber diameter.
FIGS. 9*b* and 9*c* show the expression of synemin and vimentin, respectively in astrocytes grown in cultures with different fiber diameter.
Figure 9:
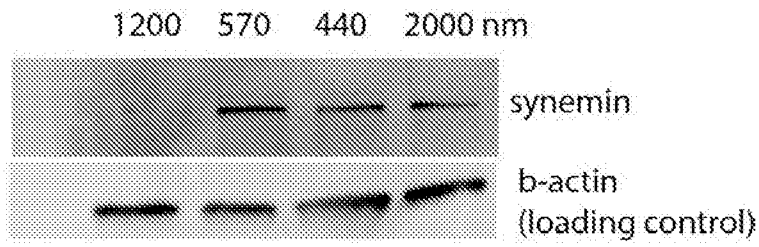
Figure 9:
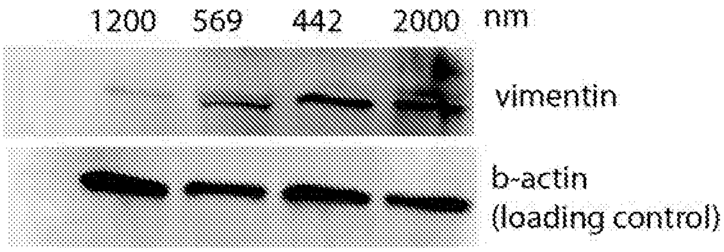

The graph in FIG. 9*a* shows the percentage of astrocytes that express GFAP (that are reactive) grown on scaffolds of different diameters. The data indicates that cells in both cultures with either larger (2000 nm) or smaller (570 nm) random oriented fiber diameters are more reactive than when grown on random oriented fiber scaffolds with a diameter of 1200 nm. Further, the Western blot analysis in FIGS. 9*b* and 9*c*, confirms that astrocytes which are grown on either 570 nm, 440 nm or 2000 nm diameter random oriented fibers increased significantly the expression of both, synemin and vimentin (two reactive astrocyte marker proteins) compared to astrocytes grown on 1200 nm diameter random oriented fiber scaffolds. B-actin is a control showing if the amount protein loaded on the gel is comparable between the different samples. Thus the inventors show that using a fiber diameter of approximate 1200 nm results in superior, stress reduced astrocyte cultures compared to cultures grown on smaller fiber diameters as used in prior art.

Figure 10:
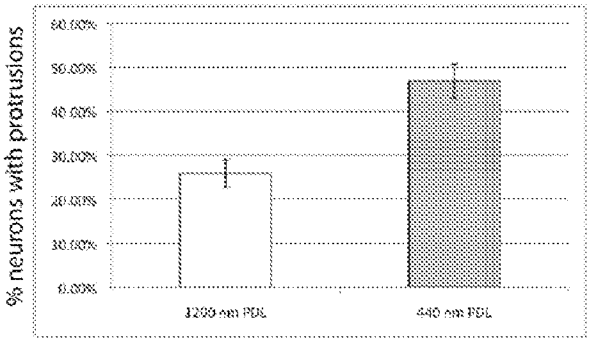
FIG. 10*a* shows a graph demonstrating the effect of fiber diameter in protrusion development of neurons.
FIGS. 10*b* and 10*c* show immunographs of Tuj-1 labeled neurites grown on randomly oriented fibers of different diameter.
Figure 10:
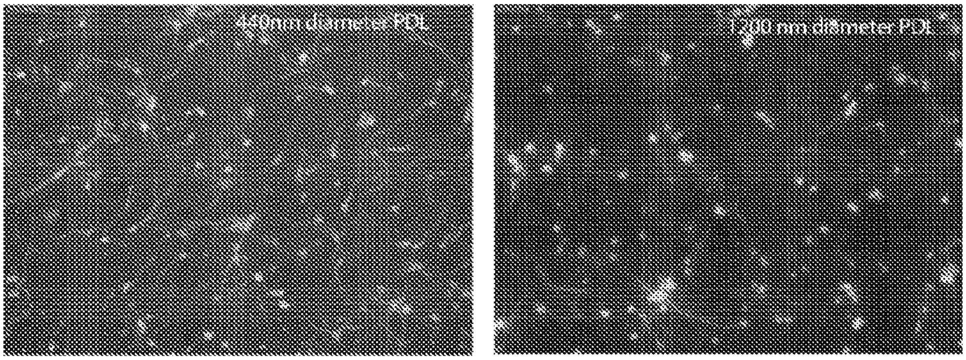

The graph in FIG. 10*a* shows the effect of fiber diameter on neuronal cell growth. Neurons were seeded on PDL coated random oriented fibers with a diameter of either 1200 nm or 440 nm. The cells were fixed and labeled for tuj-1 and image analysis of respective culture shows that neurons prefer a smaller diameter, i.e. 440 nm, compared to 1200 nm. Significantly more neurons developed proper neurites when grown on PDL coated 440 nm diameter random oriented fibers (p value<0.01).

Figure 11:
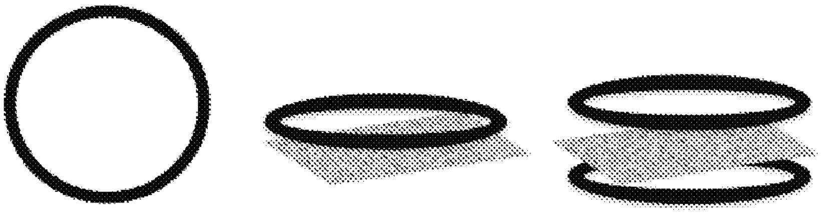
FIG. 11*a* shows a top view of a ring structure for holding the scaffold.
FIG. 11*b* and FIG. 11*c* depict perspective side views of one (FIG. 11*b*) or two (FIG. 11*c*) circular ring structures keeping the fiber scaffolds in place.

FIG. 11 show perspective views of the ring structures holding the scaffolds in place within a cell culture container. In FIG. 11*a* a top view of the structure is depicted. The fiber scaffold lays underneath the ring structure on an even surface such as the bottom of a petri-dish. In FIG. 11*b* a perspective side view of the ring structure on top of the fiber scaffold is given. FIG. 11C depicts an alternative immobilization method for the fiber scaffold, where two ring structures sandwich the fiber scaffolds to hold them in place.

Astrocytes Increase their GFAP Levels after Incubation with TGFbeta1

Methods

Electrospinning

The solutions for electrospinning are prepared by mixing 11 wt % biocompatible polyether-based polyurethane resin in a 60:40 mixture of tetrahydrofuran and n,n-dimethylformamide DMF (various amounts of NaCl can be added to increase conductivity of the solution to be able to electrospin thinner fibers). The solution is mixed with magnetic stirrer for 24 h and transferred to a syringe for electrospinning with a metal cannula. The electrospinning process parameters are: feeding rate of 2 ml/h, a positive potential of 18 kV, a 21 G cannula and a distance of 18 cm from the nozzle tip to the collector. The fibers produced under these conditions consist of an average diameter of approximately 1200 nm. The fibers are collected on a carrier such as a glass coverslips attached on aluminum foil wrapped around the grounded rotating conveyor.

To achieve the spinning of fibers with a significantly smaller diameter than 1200 nm, i.e. 450 nm, the following solutions are used:

The solutions for electrospinning are prepared by mixing 9 wt % biocompatible polyether-based polyurethane resin in a 60:40 mixture of tetrahydrofuran and n,n-dimethylformamide DMF+0.45% NaCl. The solution is mixed with magnetic stirrer for 24 h and transferred to a syringe for electrospinning with a metal cannula. The electrospinning process parameters are: feeding rate of 2 ml/h, a positive potential of 18 kV, a 27 G cannula and a distance of 18 cm from the nozzle tip to the collector.

To achieve the spinning of fibers with a significantly larger diameter than 1200 nm, i.e. 2300 nm, the following solutions are used:

The solutions for electrospinning are prepared by mixing 13 wt % biocompatible polyether-based polyurethane resin in a 60:40 mixture of tetrahydrofuran and n,n-dimethylformamide DMF. The solution is mixed with magnetic stirrer for 24 h and transferred to a syringe for electrospinning with a metal cannula. The electrospinning process parameters are: feeding rate of 2 ml/h, a positive potential of 18 kV, a 18 G cannula and a distance of 18 cm from the nozzle tip to the collector.

The fiber diameter can be adjusted by, but not limited to, changing electrospinning parameters such as voltage, distance between collector and target, solution feeding rate, needle diameter, ambient conditions such as humidity, temperature and solution parameters such as concentration, conductivity, solvent ratios, as well as the choice of solvent.

Porosity

The porosity of the fiber scaffold, i.e. air to fiber ratio within the scaffold, ranges from 60-85% open spaces with a preferred porosity of 65-75%. The fiber scaffold porosity is inevitably linked to the fiber diameter. Changes in production of the fiber diameter as described above will automatically change the scaffolds porosity. The fibers can be spun onto a substrate to be used as cell culture plate inserts. The fiber scaffolds are coated with a mixture of bio-active substrates to create a neural cell friendly environment. The porosity decreases with larger fiber diameter and increases with smaller diameter, as for example in a scaffold comprising fibers with a diameter of about 450 nm the porosity (air to volume ratio) is about 70-90% open spaces.

Coating

To coat the fibers with bio-active substrates, they are sterilized with 70% Ethanol, washed in dd$H_2O$ followed by an incubation step of either:

1. Poly-L-Ornithine: (10 μg/ml in dd$H_2O$ with 285 μl/$cm^2$ surface) for 2 h followed by three wash steps in dd$H_2O$. This first coating is followed by an incubation step with Laminin (5 μg/ml in DPBS: Dulbecco's phosphate buffered saline) with 285 μl/$cm^2$ surface) at least 2 h (POLAM).

2. Poly-D-Lysine (PDL): (10 μg/ml in DPBS with 285 μl/$cm^2$ surface) overnight incubation.

3. Collagen I: (5 μg/ml in DPBS with 285 μl/$cm^2$ surface in dd$H_2$O containing 0.02M acetic acid (final concentration), and followed by about 1 h incubation.

After additional washing with DPBS, the coating of the fibers is finished.

All incubation steps are conducted in a cell culture incubator in a humid atmosphere at 37° C. and 5% $CO_2$.

Electrospinning

The electrospinning is conducted as described above with the addition of another syringe with a metal cannula and containing the bio-active substrates in a solution. The feeding rate of the bio-active substrates is equal to the feeding rate of the polymer feeding rate during electrospinning. The electrospinning process is initiated and as the positive potential is also applied to the syringe with the metal cannula containing the bio-active substrates these are co-sprayed into the scaffold simultaneously as the fiber scaffold is formed.

The fiber scaffold can be partially of fully surface modified to enhance cell or protein adhesion to the surface. The fiber scaffolds may be treated with plasma of one or a combination of process gases to create a scaffold, which has altered surface functionalities that enables a higher degree of bioactive molecule binding to the fiber surface. The plasma treatment further etches the fiber scaffold to increase the fiber surface porosity and fiber surface roughness. To plasma treat the fiber scaffolds they are placed into a plasma etch tool and one or a combination of the following treatments are applied.

1. The fiber scaffold is subject to oxygen plasma for 15 sec using a 30 sccm gas flow, 100 mTorr process pressure, 10-6 mbar base pressure, 100 W RF electrode power. After the treatment the fiber scaffold is exposed to air to let any remaining free radicals settle.

2. The process described under point 1 may also for example be applied for 30 sec, 1, 3 or 5 min.

3. The fiber scaffold may be for example be subject to argon plasma for 15 sec using a 30 sccm gas flow, 100 mTorr process pressure, 10-6 mbar base pressure, 100 W RF electrode power. After the treatment the fiber scaffold is exposed to air to let any remaining free radicals settle.

4. The process described under point 3 may for example be applied for 30 sec, 1, 3, 5 or 10 min.

5. The fiber scaffold may for example be subject to hydrogen plasma for 3 min using a 10 sccm gas flow, 250 mTorr process pressure, 10-6 mbar base pressure, 50 W RF electrode power. After the treatment the fiber scaffold is exposed to air to let any remaining free radicals settle.

6. The process described under point 5 may be applied for 30 sec, 1, 3, 5 or 10 min.

7. The fiber scaffold is subject to Tetraflouromethaneplasma for 3 min using a 10 sccm gas flow, 250 mTorr process pressure, 10-6 mbar base pressure, 50 W RF electrode power. After the treatment the fiber scaffold is exposed to air to let any remaining free radicals settle.

8. The process described under point 7 may be applied for 30 sec, 1, 3, 5 or 10 min.

Conductive Scaffold

In another embodiment of the invention, the polyurethane fibers are partially or fully coated with conductive materials such as titanium (Ti), gold (Au), platinum (Pt), titanium plus gold, or platinum plus gold in the form of a thin or thick film to create a conductive scaffold that can be used for electrical stimulation of cells, or cell sensing purposes. These coatings allow to measure changes of conductivity within the fiber scaffold as a measurement of changes in neural cell migration, proliferation and cell death as dying cells detach and cause a change in conductivity. Similarly, proliferation of neural cells on the fiber scaffold will lead to changes in the surface area covered by cells which in turn causes changes in conductivity. To coat the fibers with conductive material one or a combination of the following methods are applied:

1. The fiber scaffold is placed into a sputter tool. The chamber is pumped down to a base pressure of <10-6 mbar. The sputter targets are any kind of conductive metals, preferably Ti, Au, or Pt. The sputtered material is deposited with a speed between 0.5-3 nm/s depending on applied substrate power. The final thickness of each individual conductive layer of the film is less than 200 nm. The process gas is an inert gas, preferably nitrogen or argon.

2. In another embodiment, the fiber scaffold is placed into a sputter down tool. The chamber is pumped down to a base pressure of 2*10-7 mbar. The Ti target is sputtered using DC magnetron sputtering with an effect of 1 kW and the Ti film is deposited onto the fiber scaffold with a rate of ~1.6 nm/s until the coating thickness is 50 nm. Nitrogen is used as process gas.

3. In another embodiment, the fiber scaffold is placed into a sputter down tool. The chamber is pumped down to a base pressure of 2*10-7 mbar. The Au target is sputtered using DC magnetron sputtering with an effect of 0.22 kW and the Au film is deposited onto the fiber scaffold with a rate of ~1.1 nm/s until the coating thickness is 50 nm. Nitrogen is used as process gas.

4. In another embodiment, both Ti and Au are sputtered according to the process described in 3.

Cell Cultures

Neural cells are seeded in their respective culture media (DMEM+10% fetal calf serum for astrocytes, neurobasal medium+1×B27 for neurons etc.) onto the fiber scaffold and incubated for 24 h to allow cells to adhere to the surface before change of medium and potential treatments are conducted. The culture conditions (i.e. atmosphere, culture media, temperature and $CO_2$ levels) for neural cell cultures on the fiber scaffolds are identical to those in standard two dimensional cell cultures.

Survival assays are conducted after neural cells have been seeded onto the scaffolds. Neural cell cultures on the fiber scaffolds are treated with a drug and compared to untreated neural cell cultures. The media supernatant of the respective neural cell cultures is harvested at different time points after treatment and standard survival assays such as the "LDH" assays (e.g. LDH cytotoxicity detection kit—TaKaRa) are conducted to investigate drug influence on cell survival.

Changes in Protein Expression Levels after Drug Treatment

To isolate the cells for further analysis the fiber scaffold with attached neural cells is removed from the scaffold holding structure after drug treatment and submerged in standard protein lysis buffer (containing glycerol, Triton-X100, EDTA, Tris-HCL, NaCl). The preparation is sonicated for 30 sec to solubilise the proteins. The protein solution can be used for Western blot assays to investigate changes in protein expression of the protein of interest after drug treatment (for Western blot methods see: Protein Blotting Guide, A Guide to Transfer and Detection, Third Edition, BIORAD homepage).

The effects of drug treatments on neural cells as mentioned above may be investigated with the help of standard immunocytochemistry assays. After incubation of the neural cell cultures grown on the fiber scaffold, the cell cultures are washed in PBS (Phosphate Buffered Saline) followed by cell fixation with 4% PFA (paraformaldehyde). After additional wash steps and incubation with antibodies against the proteins of interest these proteins are labeled with fluorophor-linked antibodies. This allows for microscopy images of the proteins of interest to be taken and to be compared to images from non-drug treated three dimensional neural cell cultures (for methods see: e.g. "Immunocytochemistry—A practical approach", Oxford University press, 1993, ISBN 0-19-963271-7)

Finally, the present invention provides a solution that counteracts the drawbacks obtained by prior art by providing a three dimensional biocompatible scaffold designed for neural cell cultures, method of the same and with a novel and inventive screening system.

Other features and uses of the invention and their associated advantages will be evident to a person skilled in the art upon reading the description and the examples.

REFERENCES

Cukierman, E., R. Pankov, et al. (2001). "Taking Cell matrix adhesions to the third dimension." Science 294(5547): 1708-1712.

Lee, J., M. J. Cuddihy, et al. (2008). "Three-dimensional Cell culture matrices: state of the art." Tissue Eng Part B Rev 14(1): 61-86.

Mueller-Klieser, W. (1997). "Three dimensional Cell cultures: from molecular mechanisms to clinical applications." Am J Physiol 273(4 Pt 1): C1109-1123.

Walpita, D. and E. Hay (2002). "Studying Actin dependent processes in tissue culture." Nat Rev Mol Cell Biol 3(2):137-141.

The invention claimed is:

1. A biocompatible scaffold for three dimensional cultivation of cells, the scaffold comprising:

one or more fibers randomly oriented to form a three dimensional scaffold with open spaces for cultured cells, and a bio-active coating comprising poly-L-ornithine+laminin (POLAM) on the one or more fibers, wherein the randomly oriented fibers have a diameter of 1100-1300 nm.

2. A biocompatible scaffold comprising: one or more fibers randomly oriented to form a three dimensional scaffold with open spaces for cultured cells, wherein the randomly oriented fibers have a diameter of 1100-1300 nm, a bio-active coating comprising poly-L-ornithine+laminin (POLAM) on the one or more fibers, and astroglia (astrocytes) cultured in the open spaces.

3. The biocompatible scaffold according to claim 1, wherein the one or more fibers comprise electrospun polymer fibers.

4. The biocompatible scaffold according to claim 1, wherein the one or more fibers comprise a polymer selected from the group consisting of polyether-based polyurethane, polystyrene (PS), poly acrylo nitrile (PAN), poly carbonate (PC), polyvinylpyrrolidone (PVP), polybutadiene, polyvinyl butyral (PVB), poly vinyl chloride (PVC), poly vinyl methyl ether (PVME), poly lactic-co-glycolic acid (PLGA), poly(l-lactic acid), polyester, polycaprolactone (PCL), poly ethylene oxide (PEO), polyaniline (PANI), polyflourenes, polypyrroles (PPY), poly ethylene dioxythiophene (PEDOT), and mixtures thereof.

5. A biocompatible scaffold for three dimensional cultivation of cells, the scaffold comprising: one or more electrospun polymer fibers randomly oriented to form a three dimensional scaffold with open spaces for cultured cells, and a bio-active coating comprising poly-L-ornithine+laminin (POLAM) on the one or more fibers, wherein the randomly oriented fibers have a diameter of 1100-1300 nm, and wherein the one or more fibers comprise polyether-based polyurethane.

6. The biocompatible scaffold according to claim 3, wherein the one or more fibers form a scaffold having a porosity that corresponds to 60-95% open spaces.

7. The biocompatible scaffold according to claim 3, further comprising an electrically conductive material disposed between the fiber polymer and the bio-active coating.

8. The biocompatible scaffold according to claim 7, wherein the electrically conductive material comprises a sputter coating of titanium or platinum or gold, wherein the sputter coating has a thickness less than 200 nanometers.

9. The biocompatible scaffold according to claim 1, further comprising aligned fibers, wherein the scaffold comprises a mixture of randomly oriented and aligned fibers.

10. The biocompatible scaffold according to claim 9, wherein the aligned fibers further comprise a sputter coating of electrically conductive material.

11. The biocompatible scaffold according to claim 3, wherein the fibers are plasma treated before coating with bio-active substrates.

12. A cell culture system comprising:

a container to hold cells, a cell culture media in the container, and a biocompatible scaffold according to claim 1 disposed in the container, and astroglia cells (astrocytes) attached to the scaffold.

13. The cell culture system according to claim 12 further comprising a substrate disposed within the container, wherein the biocompatible scaffold is attached to or disposed on a surface of the substrate.

14. The cell culture system according to claim 12 further comprising a containment structure of inert material placed within the container to immobilize the biocompatible scaffold.

15. The cell culture system according to claim 14, wherein the containment structure is in the shape of a ring or two rings holding the biocompatible scaffold in place.

16. A method of culturing cells comprising:

seeding a biocompatible scaffold according to claim 1 with astroglia cells (astrocytes), adding culture media; and incubating the resultant three dimensional culture under conditions suitable for attachment of the astrocytes to the biocompatible scaffold and growth of the cells.

17. The method according to claim 16, wherein said cells further comprise at least one cell type selected from neurons, oligodendrocytes, and Schwann cells.

18. The method of claim 17, said method further comprising the steps of: culturing the three dimensional cell culture in the presence and absence of a test agent; and determining effects of the test agent on the cells by comparing cellular events in the cells grown in the presence of the agent versus in the absence of the agent.

19. The biocompatible scaffold according to claim 1, wherein the fibers have a diameter of about 1200 nm.

* * * * *